(12) United States Patent
Schulz et al.

(10) Patent No.: US 9,696,229 B2
(45) Date of Patent: Jul. 4, 2017

(54) PRECISION FORCE APPLICATOR FOR FORCE TRANSDUCER CALIBRATION

(71) Applicant: MTS Systems Corporation, Eden Praire, MN (US)

(72) Inventors: Bradley Dean Schulz, Savage, MN (US); Paul M. Krueger, Maple Grove, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 283 days.

(21) Appl. No.: 14/508,754

(22) Filed: Oct. 7, 2014

(65) Prior Publication Data

US 2015/0096348 A1    Apr. 9, 2015

Related U.S. Application Data

(60) Provisional application No. 61/887,753, filed on Oct. 7, 2013.

(51) Int. Cl.
| | | |
|---|---|---|
| *F16D 1/04* | (2006.01) | |
| *G01L 25/00* | (2006.01) | |
| *G01L 5/00* | (2006.01) | |

(52) U.S. Cl.
CPC ............ *G01L 25/00* (2013.01); *G01L 5/0028* (2013.01); *F16D 1/04* (2013.01); *G01N 2203/021* (2013.01)

(58) Field of Classification Search
CPC ........................................................ F16D 1/04
See application file for complete search history.

(56) References Cited

U.S. PATENT DOCUMENTS

| 1,332,491 A | 3/1920 | Figari |
| 3,402,613 A | 9/1968 | Neusel et al. |

(Continued)

FOREIGN PATENT DOCUMENTS

| CN | 203036476 U | * 7/2013 | .............. F21V 29/90 |
| GB | 1260704 A |   1/1972 | |

(Continued)

OTHER PUBLICATIONS

International Search Report and Written Opinion for corresponding foreign application PCT/US2014/059493 filed Oct. 7, 2014.

(Continued)

*Primary Examiner* — Jill Culler
*Assistant Examiner* — Ruben Parco, Jr.
(74) *Attorney, Agent, or Firm* — Steven M. Koehler; Westman, Champlin & Koehler, P.A.

(57) ABSTRACT

A force applicator assembly is disclosed to calibrate an in-situ force transducer (or load cell) in a force (load) applying test machine. The force applicator includes stationary member configured to be secured to fixed structure, a moving member, a load cell operably coupled to an end of the moving member, and a differential screw assembly connecting the moving member to the stationary member. A coupling assembly can be used to assure that only tension or compression loads are applied. The coupling assembly can be configured if desired such that no tension or compression loads can be applied. A method to calibrate an in-situ force transducer in a force applying test machine is also provided and uses a force generator and the coupling assembly.

20 Claims, 8 Drawing Sheets

(56) References Cited

U.S. PATENT DOCUMENTS

| | | |
|---|---|---|
| 3,525,140 A | 8/1970 | Cachon |
| 4,501,153 A | 2/1985 | Mehes |
| 2011/0101864 A1* | 5/2011 | Ku .................... F21V 29/90 315/115 |
| 2012/0167657 A1 | 7/2012 | Bormann |

FOREIGN PATENT DOCUMENTS

| | | | |
|---|---|---|---|
| JP | 2002295497 A | * 10/2002 | ............... F16D 1/04 |
| WO | 8202949 | 9/1982 | |
| WO | 2011012182 | 2/2011 | |

OTHER PUBLICATIONS

Invitation to Pay Additional Fees for corresponding International application No. PCT/US2014/059493, filed on Oct. 7, 2014, mailed on Mar. 4, 2015.

* cited by examiner

PRECISION FORCE APPLICATOR FOR FORCE TRANSDUCER CALIBRATION

CROSS-REFERENCE TO RELATED APPLICATION

This application claims the benefit of U.S. Provisional Application Ser. No. 61/887,753, filed Oct. 7, 2013, having the same title, and is hereby incorporated by reference in its entirety.

BACKGROUND

The discussion below is merely provided for general background information and is not intended to be used as an aid in determining the scope of the claimed subject matter.

Force measuring transducers require periodic calibration via comparison of the transducer under test to a reference standard transducer. Calibration must be performed at a range of incremental forces, per international standards. In many cases, the testing machine for performing the test can be used as the force applicator for calibration purposes; however, in some situations this is not possible or the resulting fixturing needed to perform the calibration introduces an unacceptable error.

In one such case, an electrodynamic driven material testing system has the unique characteristic that its short term dynamic force capability exceeds its static force. Its dynamic rated force can be maintained for a duration shorter than required for calibration. Therefore, an alternate means of force application is required to achieve the full range.

In other systems, the controller or control system is not capable of performing the test needed for calibration. Likewise, the structure of some systems do not allow for in-situ calibration. For those machines that allow in-situ calibration, the coupling and fixturing technologies currently used are not accurate enough for the latest high accuracy standards that must be met. Although methods and apparatuses have been used to apply external loads, these have proven incapable of producing repeatable results with high accuracy.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

A first aspect disclosed is a force applicator assembly to calibrate an in-situ force transducer (or load cell) in a force (load) applying test machine. The force applicator includes a stationary member configured to be secured to a fixed structure, a moving member, a load cell operably coupled to an end of the moving member, and a differential screw assembly connecting the moving member to the stationary member.

A second aspect disclosed is a force applicator assembly to calibrate an in-situ force transducer (or load cell) in a force (load) applying test machine. The force applicator includes a reaction frame having a base configured to mount proximate the in-situ force transducer. A vertical support is secured to the base and a cross-head is secured to the vertical support. A stationary member is secured to the cross-head. A differential screw assembly connects a moving member to the stationary member.

One or more of the following features can be included in each of the aspects above as desired, if not otherwise provided, to provide further embodiments.

The differential screw assembly can include a rotatable member threadably connected to the moving member with a first set of threads having a first thread pitch. The rotatable member is also threadably connected to the stationary member with a second set of threads having a second thread pitch, the second thread pitch being different than the first thread pitch. The moving member can comprise a threaded rod, while the rotatable member can comprise a tube having a threaded bore comprising the first set of threads. In this embodiment, the tube has an outer surface having the second set of threads that are threadably connected with the stationary member. In another embodiment, the moving member and the stationary member each comprise threaded rods that are aligned with each other. The rotating member engages the threads of each of the threaded rods. Rotation of the rotating member causes linear movement of the moving member threaded rod relative to the stationary member threaded rod.

An anti-rotate device can be provided that is connected to the stationary member and is connected to the moving member and configured to inhibit at least rotation of the moving member, or rotation of the both the stationary member and the moving member. The anti-rotate device can be a recess formed in the moving member and a pin secured to the stationary member and extending in the recess. Likewise, the anti-rotate device can be a recess formed in the stationary member and a pin secured to the moving member and extending in the recess. Each recess can function as a guide for the pin.

The first aspect can also include a reaction frame having a base configured to mount proximate the in-situ force transducer. A vertical support is secured to the base and a cross-head is secured to the vertical support. The stationary member is secured to the cross-head.

In another embodiment, a coupling assembly can be operably connected to the moving member. The coupling assembly has a distal end remote from the moving member. The coupling assembly is configured to align an axis of the moving member with an axis of the distal end when forces are transferred through the coupling assembly.

Another aspect disclosed is a coupling assembly to couple a first element to a second element to transfer linear compression and/or tension forces. The coupling assembly includes a retainer assembly connectable to the first element having a first member having a first three dimensional curved surface and a second member having a second three dimensional curved surface spaced apart from and facing the first three dimensional curved surface. A reaction structure is connectable to the second element and is disposed between the first and second three dimensional curved surfaces. The reaction structure has spacing between the first and second three dimensional curved surfaces such that the reaction structure contacts only one of the first or second three dimensional surfaces when transmitting forces therebetween.

One or more of the following features can be included in each of the first, second and third aspects above as desired, if not otherwise provided, to provide further embodiments.

The coupling assembly can be used to connect the moving member to the load cell, while the distal end is configured to be connected to the in-situ force transducer.

The retainer assembly can include at least one aperture, the reaction structure extending through the aperture. If desired, two opposed apertures can be provided, the reaction structure extending through each of the apertures. Each of first and second three dimensional curved surfaces can comprise at least a partial ball. The reaction structure can include opposed concave surfaces, each concave surface engaging one of the three dimensional curved surfaces.

Another aspect disclosed is a method to calibrate an in-situ force transducer in a force applying test machine. The method includes mounting a reference load cell and a coupler so as to obtain a load path between a force generator (e.g. force applicator described above or a force generating device on the testing machine such as an actuator) and the in-situ force transducer, the coupling assembly comprising a reaction structure and a first member configured to selectively engage one side of the reaction structure and a second member configured to selectively engage a side of the reaction structure that faces in a direction opposite to said one side; and operating the force generator so as to configure a first space between the first member and the reaction structure and also a second space between the second member and the reaction structure. Any of the foregoing features described above can be used in the method as desired.

DETAILED DESCRIPTION OF ILLUSTRATIVE EMBODIMENTS

Figure 1:
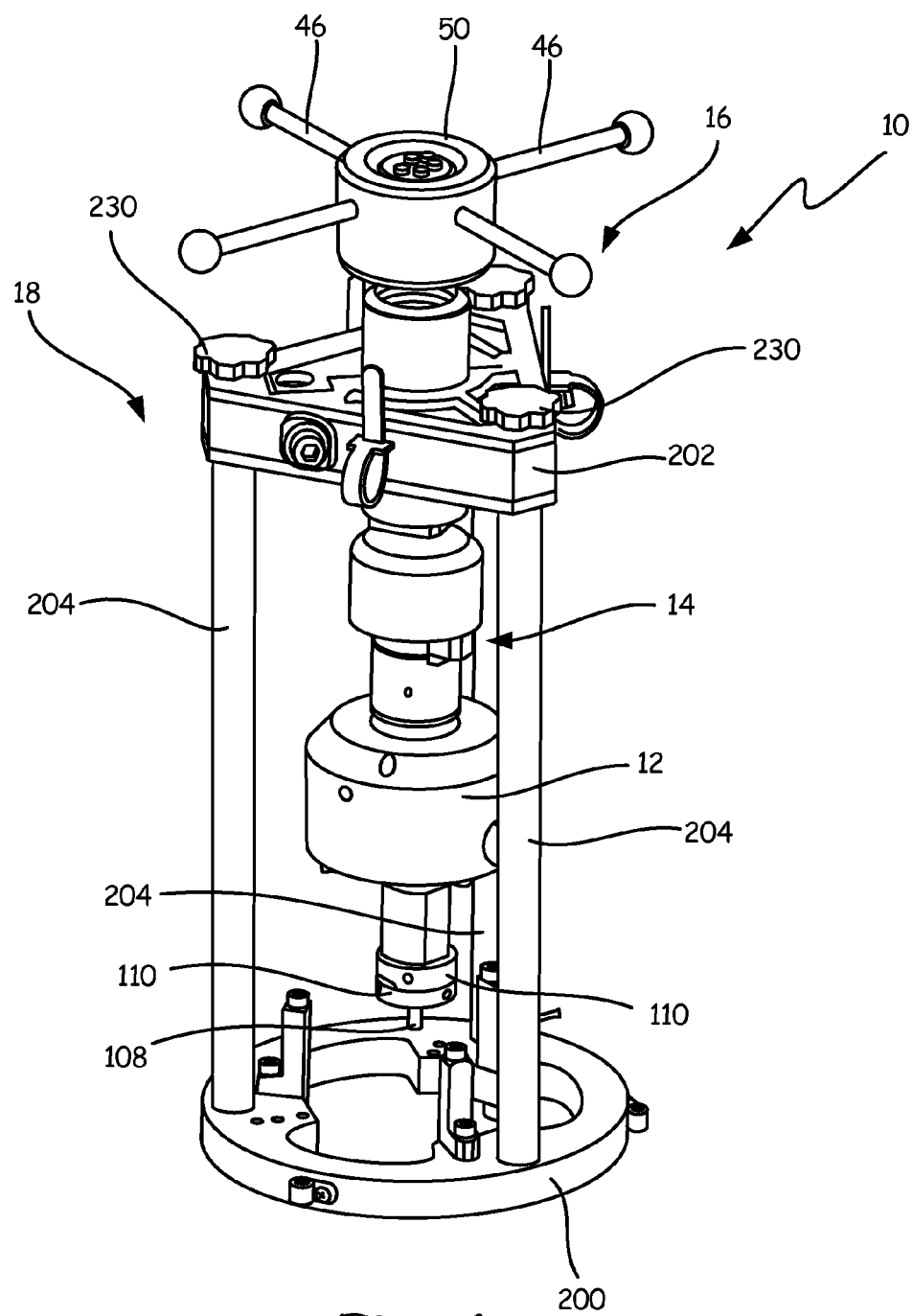
FIG. 1 is a perspective view of a force applicator assembly.

Aspects of the invention include but are not limited to a precision force applicator assembly having a force applicator 10 for generating precision forces on a load cell 12, herein a reference standard; however, the specific type of load cells described herein do not form any part of the invention. An innovative coupler or coupling assembly 14 is also illustrated in the figures and can be used to couple forces between the force applicator 10 and the load cells as described below. The force applicator 10 includes an actuator 16, which is typically supported so as to apply loads to the load cell 12 (and a load cell under test 102 in FIG. 3) by a reaction frame 18.

Figure 3:
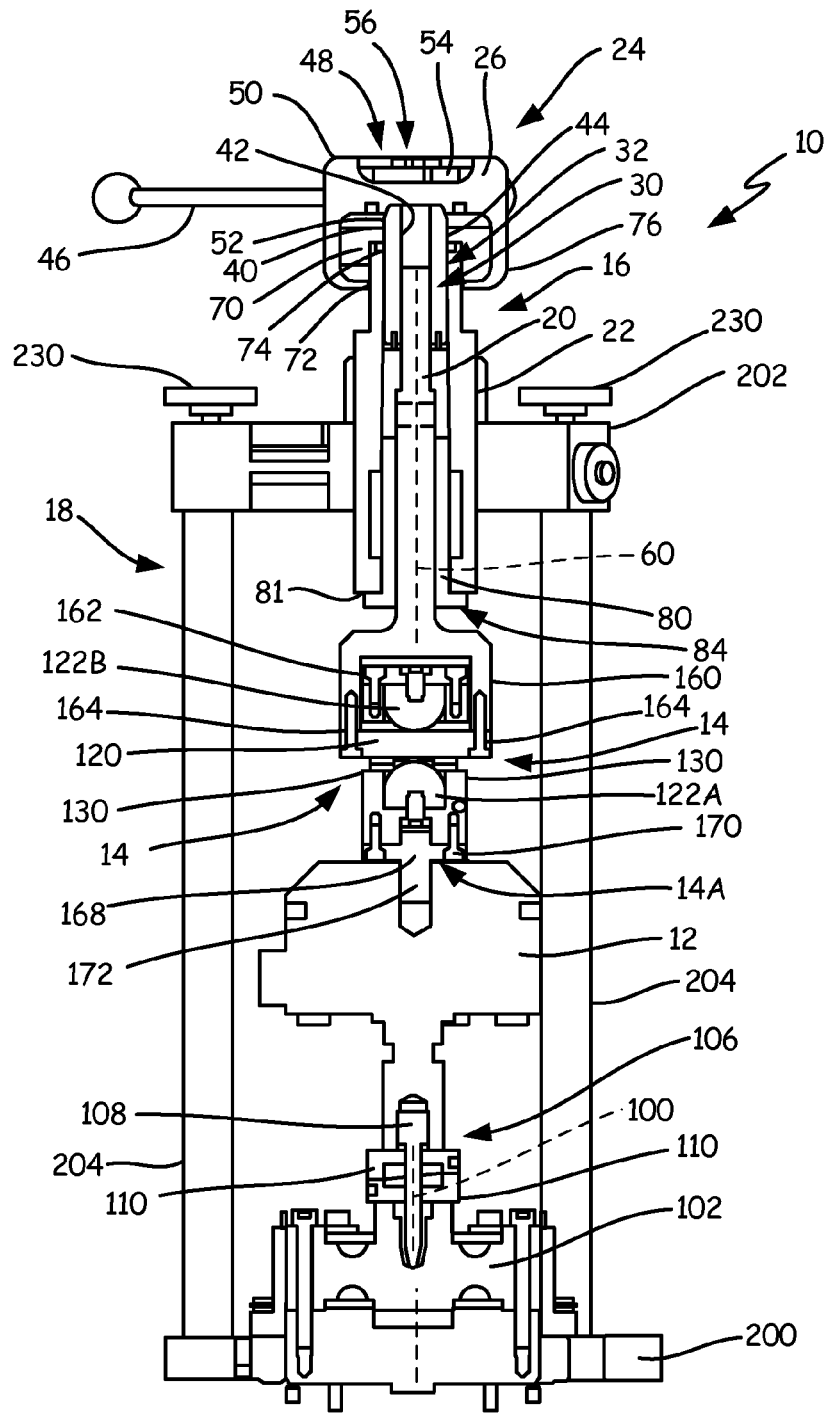
FIG. 3 is a sectional view of the force applicator assembly.
Figure 6:
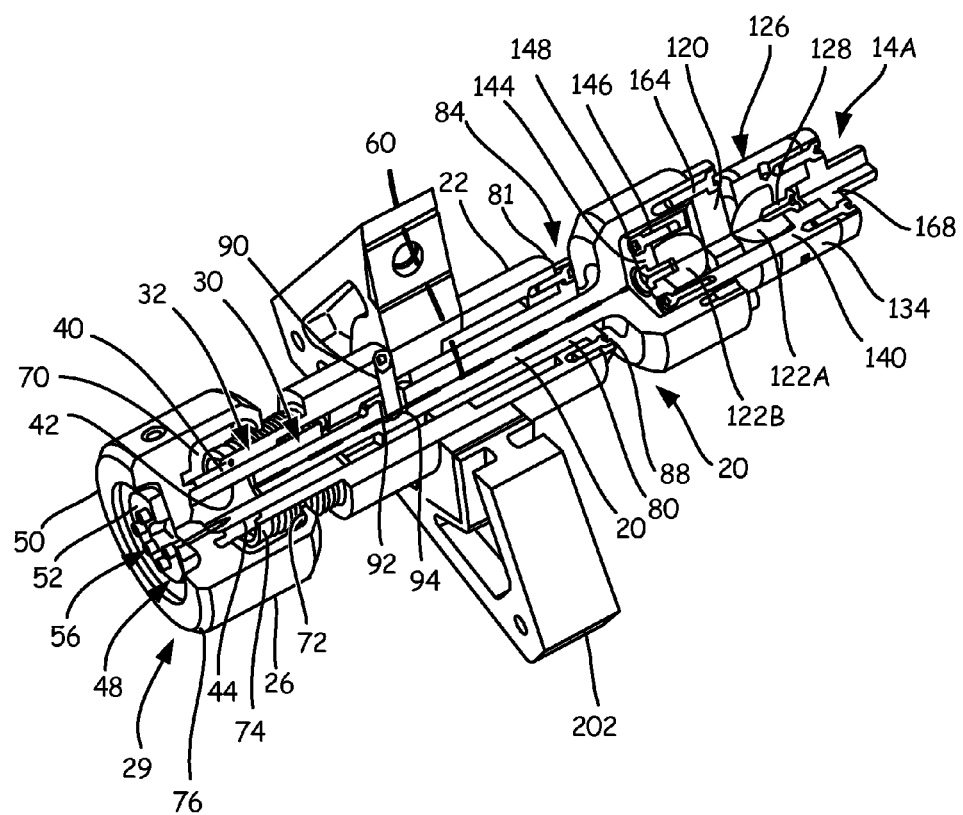
FIG. 6 is a perspective view of a portion of the force applicator assembly with portions removed.

Referring to FIGS. 3 and 6, the actuator 16 includes a moving member 20, herein illustrated as an actuator rod that moves with respect to a stationary member 22, herein embodied as a support tube. A differential screw assembly 24 couples the moving member 20 to the stationary support or member 22 and causes the moving member 20 to be displaced relative thereto by rotation of a rotatable force receiving member 26. The differential screw assembly 24 includes the force receiving member 26 which is threadably coupled to the moving member 20 with a first set of threads 30 having a first thread pitch. The force receiving member 26 is in addition threadably coupled to the stationary member 22 with a second set of threads 32 having a second thread pitch, the second thread pitch being different than the first thread pitch. Both the moving member 20 and the stationary support 22 are inhibited from rotation. When the force receiving member 26 is rotated, the moving member 20 translates relative to the stationary support 22 by an amount equal to the differential between the first and second thread pitches. The result is a very small translation of movement of the moving member 20 for a relatively large amount of rotation of the force receiving member 26; hence, the force applicator 10 can provide selected forces with high accuracy and repeatability. The first thread pitch can be coarser than the second thread pitch, or the second thread pitch can be coarser than the first thread pitch. In an exemplary embodiment, the difference in threads can be in the range of 0.0001 to 0.008 inches. Stated in terms of operation of the force receiving member 26, and not necessarily correlated to the preceding range given, in an exemplary embodiment rotation of the force receiving member 26 from no load to full load can be in a range of ½ turn (no load to full load) to 10 turns (no load to full load).

In the embodiment illustrated, the force receiving member 26 includes a shaft 40 having an internal bore 42 that includes the first set of threads 30. An outer surface 44 of the shaft 40 includes the second set of threads 32. The shaft 40 is rotated so as to cause translation of the moving member 20 due to the difference in pitch between the first set of threads 30 and the second set of threads 32. At least one radially extending handle 46 is secured to an end 48 of the shaft 40. In the embodiment illustrated, an enlarged knob member 50 couples the handle 46 to the shaft 40. The shaft 40 extends through a central aperture 52 provided in the knob 50. The end 48 of the shaft includes an extending flange 54 that is fastened to the knob 50 with suitable fastener(s) such as threaded bolt(s) 56.

Being fastened to the shaft 40, the knob 50 will rotate as well as move axially along a central axis 60 relative to the stationary support 22. The knob 50 includes an enlarged recess 70 therein with an access aperture 72. An end 74 of the stationary member 22 extends into the recess 70 through the access aperture 72, while the shaft 40 extends through the recess 70 and out of the access aperture 72 and into the stationary member 22, herein comprising a tube. The outer walls 76 of the knob 50 forming the recess 70 inhibit contaminants from reaching the second set of threads 32, while the first set of threads 30 are sealed from contaminants from the moving member 20 being disposed in the bore 42 and wherein an elongated bushing 80 seals a second end 84 of the tube 22, while providing a stable guide surface for the moving member 20, which extends into a bore of the stationary member 22. In the embodiment illustrated, the bushing 80 is secured to end 84 of the tube 22 with suitable fastener(s) herein exemplified as threaded bolt(s) 88.

An anti-rotation member 90 is provided to inhibit rotation of the moving member 20. Generally, the anti-rotation member 90 is operable coupled to the moving member 20 and a stationary member. In the embodiment illustrated in FIG. 6, the anti-rotation member 90 comprises an extending element such as a pin 90 that is secured to the stationary support 22. Herein, the pin 90 is threadably mounted to the stationary support 22. A portion 92 of the pin 90 extends into an enlarged recess or slot 94 of the moving member 20. The recess 94 is configured so as to receive the pin 90 and inhibit rotation of the moving member 20 due to the pin 90 contacting inner radial walls of the recess 94, while allowing translational movement of the moving member 20 relative to the stationary pin 90 over a limited distance. A suitable lubricant can be provided between the pin 90 and walls of the recess 94 to minimize friction for translational movement of the moving member 20.

Figure 7:
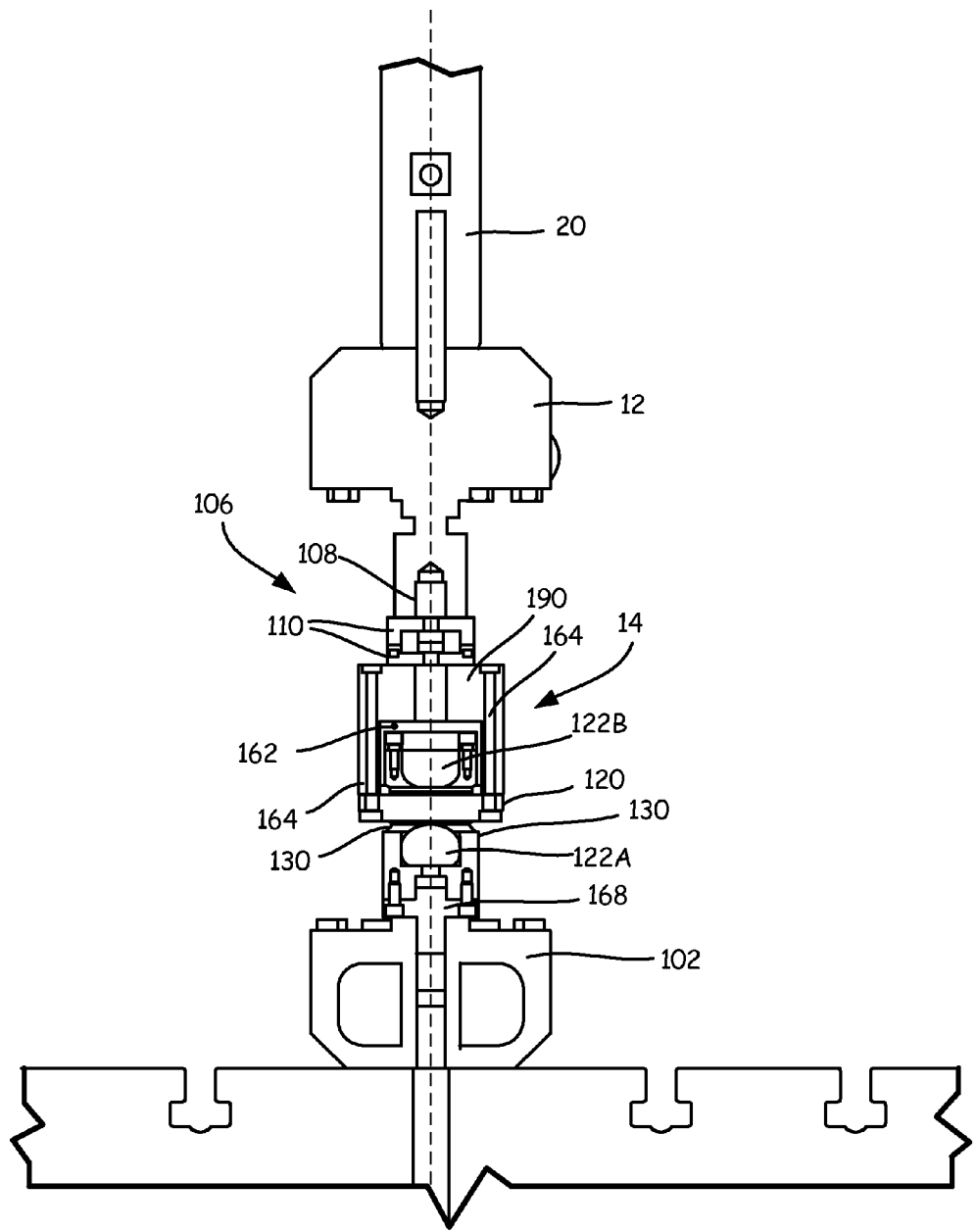
FIG. 7 is a sectional view of a force applicator assembly without a reaction frame.

FIG. 7 illustrates an embodiment that does not include the reaction frame 18, where instead the parent or test machine cross-head (moving or stationary) or other element such as the actuator assembly or other portion of the test machine frame 205 comprises the reaction structure, any one of these elements being the element that the force applicator 10 is mounted to.

Figure 9:
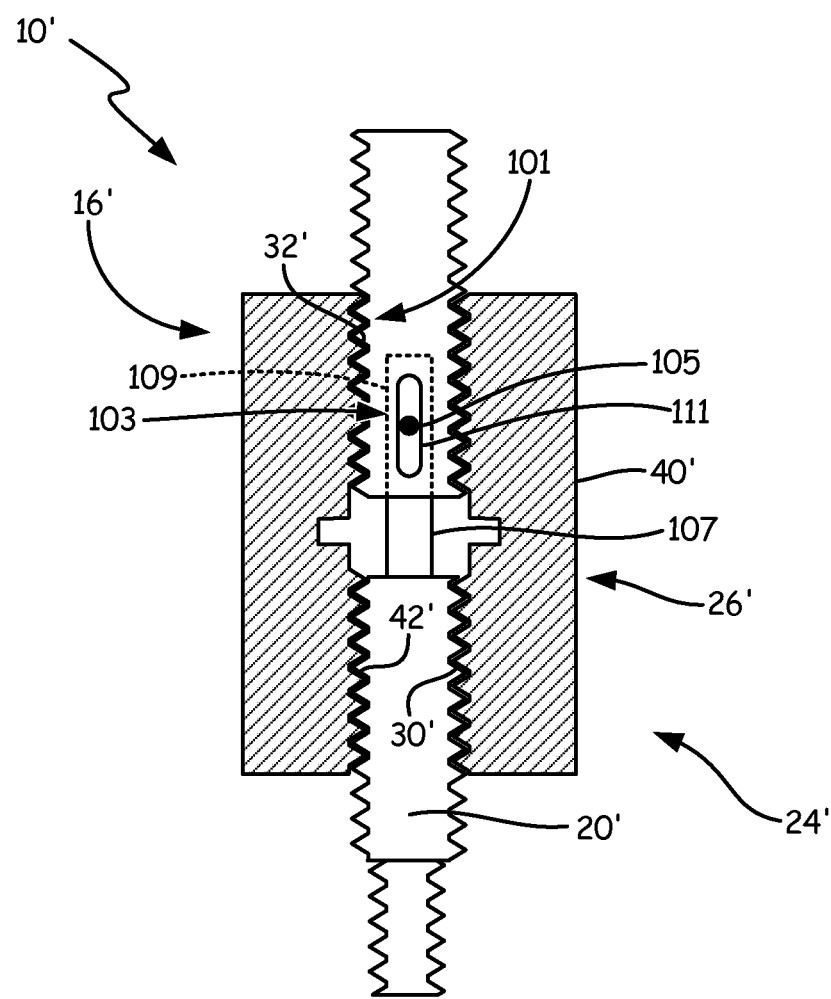
FIG. 9 is a schematic view of the second embodiment of the force applicator.

FIG. 9 illustrates a force applicator 10' that also includes a first set of threads having a first thread pitch 30' and a second set of threads 32' having a second thread pitch in a differential screw assembly 24'. A rotatable force receiving member 26' includes a rotatable shaft 40' having threaded bore 42' (herein with two thread pitches) to form an actuator 16'. In the embodiment illustrated, the rotatable shaft 40' is integral being formed of a single unitary body. As appreciated by those skilled in the art, the shaft 40' can be formed from separate parts that are then joined together.

A moving member 20' comprises a threaded rod. In operation, a threaded rod 101 comprises the stationary member and is joined to a reaction structure like either frame 18 or a part of the parent test machine as illustrated in the exemplary embodiment of FIG. 8. Rotation of the shaft 40' causes the threaded rod 20' to move downwardly due to the difference in thread pitch. An anti-rotate device inhibits rotation of the moving member 20' and herein comprises a coupling 103 between moving member 20' and rod 101 that inhibits rotation of the moving member 20'. The coupling 103 comprises a pin and guide coupling wherein pin(s) 105 are connected to one of the moving member 20' or rod 101 (herein by example moving member 20' with a portion 107 extending into a bore 109 provided in the rod 101), while the guide or recess 111 is provided in the other (herein rod 101).

Aspects of the coupler 14 will now be described. It should be noted that the coupler 14 can provide advantageous features when used with the force applicator 10, but use of the coupler 14 is not required in that the force applicator 10 can be used without the coupler 14 if desired.

The coupler 14 is operably connected (directly or indirectly) to the moving member 20 and has a distal end 14A remote from the moving member 20. The coupler 14 aligns central axis 60 of the moving member 20 so as to be aligned with a central axis 100 of a load cell 102 that is being calibrated, or is configured to align an axis of the moving member 20 with an axis of the distal end 14A when forces are transferred through the coupler 14. In other words, the coupler 14 minimizes any radial offset that might exist between the axes 60 and 100, which would cause the force applicator to apply an overturning moment to the load cell 102. In the embodiment of FIG. 3, the load cell 102 is fixably coupled to the reference load cell 12 that in turn is coupled to the moving member 20 via the coupler 14. An interface coupling 106 ensures that the load cell 112 is properly aligned with load cell 102. In the embodiment illustrated, the interface coupling 106 includes a stud 108 and spiral washers 110.

Generally, the coupler 14 includes a force reaction structure 120 operably coupled to the moving member 20, 20' or the stationary member 22. The reaction structure 120 can be connected to the moving member 20, 20'. The reaction structure 120 is disposed between reaction members 122A and 122B, each having a three dimensional curved surface that selectively engages the reaction structure 120 depending on the direction of force being transferred through the coupler 14. In the embodiment illustrated, the three dimensional curved surface on the reaction members 122A and 122B comprises partial spherical balls.

A retainer 126 supports each of the three dimensional curved surface reaction members 122A and 122B (hereinafter "three dimensional curved member") that face each other on opposite sides of the reaction structure 120. In the embodiment illustrated, the three dimensional curved member 122A is secured to the retainer 126 with a suitable fastener such as a threaded bolt 128. The reaction structure 120 extends through apertures 130 in the retainer 126 on opposite sides thereof. In the exemplary embodiment, the retainer 126 includes a cylindrical portion 134 having the apertures 130. The first three dimensional curved member 122A is secured to the cylindrical component 134, being disposed in a recess 140 thereof. The second three dimensional curved surface member 122B is secured to a cap member 144 that in turn is secured to an end 146 of the cylindrical portion 134 with suitable fastener(s) herein comprising threaded bolt(s) 148.

The reaction structure 120 selectively engages and bears against one of the three dimensional curved members 122A or 122B in order to transfer force to the load cell 102 under test. In particular, with respect to the embodiments of FIGS. 3 and 7, a compression force is applied to the load cell 102 under test by movement of the moving member 20 downwardly such that the reaction structure 120 engages the three dimensional curved member 122A. In contrast, a tension force is applied to the load cell 102 when the moving member 20 moves upwardly so that the reaction structure 120 engages the three dimensional curved member 122B.

In one embodiment, the distance between the three dimensional curved member 122A and 122B is greater than the width of the reaction structure 120 and configured with the difference in the thread pitch between the first set of threads 30 and the second set of threads 32 such that substantial angular movement of the shaft 24 is needed so that the reaction structure 120 disengages or releases from one of the three dimensional curved members 122A, 122B until it engages the other three dimensional curved member 122A, 122B. In a particularly advantageous embodiment, a near revolution or multiple revolutions of the shaft 124 are needed in order to move the moving member 20 such that the reaction structure 120 disengages from one of the three dimensional curved members 122A, 122B before the reaction structure 120 engages the other three dimensional curved member 122A, 122B. In this manner, highly accurate and repeatable forces can be generated in view of the large angular movement needed by the shaft 40. In addition, a neutral point can be obtained easily where the reaction structure 120 neither engages the three dimensional curved member 122A or the three dimensional curved member 122B. When multiple revolutions are needed by the shaft 40 to fully translate the reaction structure 120 from one of the three dimensional curved members 122A to the other three dimensional curved member 122B, the shaft 40 can be easily rotated to a position where the reaction structure 120 does not contact either of the three dimensional curved members 122A or 122B.

Figure 4A:
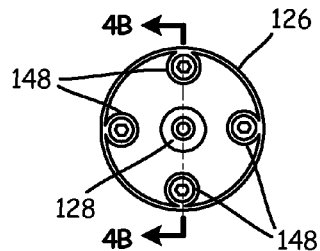
FIG. 4A is a plan view of a coupler for transferring forces.
Figure 4B:
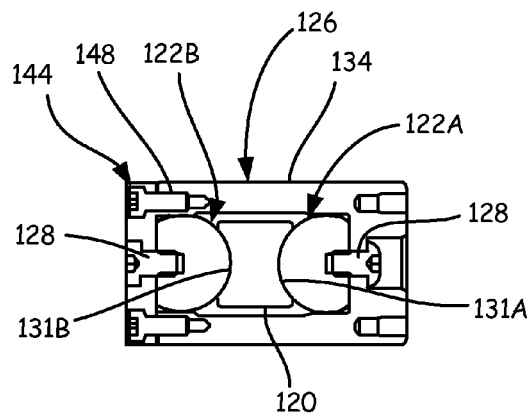
FIG. 4B is a sectional view of the coupler taken along lines 4B-4B in FIG. 4A.

The coupler 14 is also illustrated in FIGS. 4A, 4B, 5 and 6. In these figures, it is illustrated that the pair of opposing three dimensional curved members 122A and 122B load against the reaction structure 120. Although not appearing in the figures, there is a small amount of clearance or space between the curved members 122A, 122B and reaction structure 120. This assures that only pure tension or pure compression is applied to the load cells 12, 102. In particular, the moving member 20 translates either tension or compression forces to the reaction structure 120, which can comprise a hardened bar. The reaction structure 120, in turn, transfers force to either one of the three dimensional curved members 122A, 122B. Due to the space between the curved members 122A, 122B and reaction structure 120 it is also easy to configure the force applicator 10, or any force applying device such as an actuator assembly, such that clearance or space is provided between the curved members 122A, 122B and reaction structure 120 so as to obtain an operating state where no force (tension or compression) is being transferred through the coupler 14 since the presence of the space between the curved members 122A, 122B and reaction structure 120 has decoupled the force applying device from the element connected to the other side of the coupler 14. In one embodiment, the coupling assembly 14 is configured such that it is easy to see the spaces between the curved members 122A, 122B and reaction structure 120 when any force generator connected thereto is operated to achieve such spaces. As illustrated in FIG. 4B, the reaction structure 120 can include opposed concave surfaces 131A and 131B each of which receives one of the three dimensional curved members 122A or 122B.

In the embodiment illustrated in FIG. 3, the moving member 20 includes an enlarged end member 160 having a recess or cavity 162 of size so as to receive the cap member 144 and a portion of the retainer 126 attached thereto. The recess or cavity 162 is of size so as not to contact either of these parts. The reaction structure 120 is connected to the enlarged end member 160 with suitable fasteners(s) such as threaded bolt(s) 164. An end of the retainer 126 opposite the cap member 144 is secured to the load cell 102 with an interface standoff 168 that is secured to the retainer 134 with suitable fastener(s) such as threaded bolt(s) 170. The standoff 168 is threadably secured to the load cell 104 with portion 172.

In the embodiment of FIG. 7, the standoff 168 is threadably coupled to the load cell under test 102, while the reaction structure 120 is secured to a support 190 having the recess or cavity 162. The support 190 is secured to the load cell 12 opposite the moving member 20. Hence, in this configuration, the reaction structure 120 is operably connected to the moving member 20 directly (FIG. 3) or indirectly through the load cell 12 (FIG. 7) and the retainer is operably connected to the in-situ load cell 102. In another embodiment, the reaction structure 120 can be operably connected to the in-situ load cell 102 and the retainer 126 can be operably connected to the moving member 20.

Figure 8:
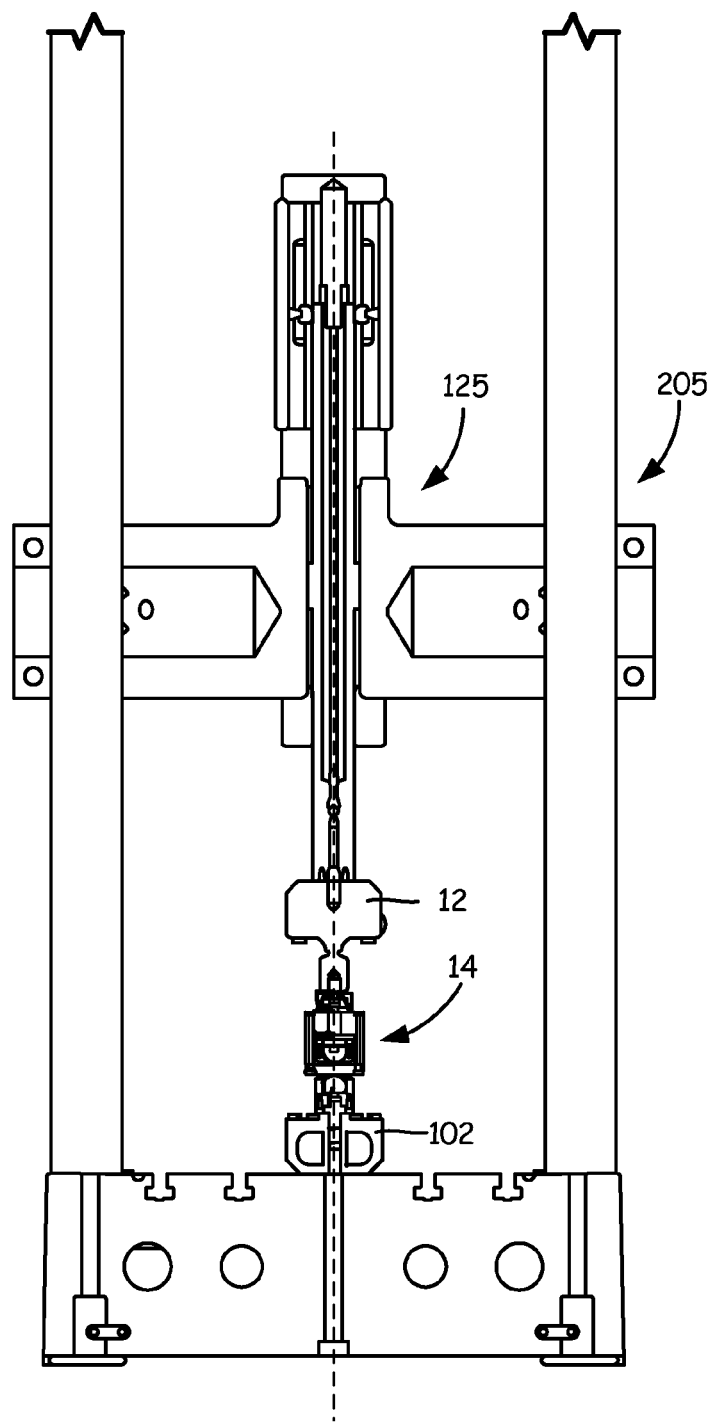
FIG. 8 is a schematic view of a second embodiment of a force applicator assembly.

FIG. 8 illustrates that the coupler 14 can be used in another exemplary calibration situation for calibrating a load cell 102. In this embodiment the force applicator 10 is not present, but rather the test machine actuator assembly 125 that provides the calibration loads to calibrate the load cell 102.

It should be noted that use of the coupler 14 is not limited to calibrating load cells. The coupler 14 can be used in other force applying systems, particularly those that need alignment of compression and/or tension loads between two members. The coupler 14 is unable to transmit significant torque. The first member is connected to the reaction structure 120, while the second member is connected to the retainer 126.

Figure 2:
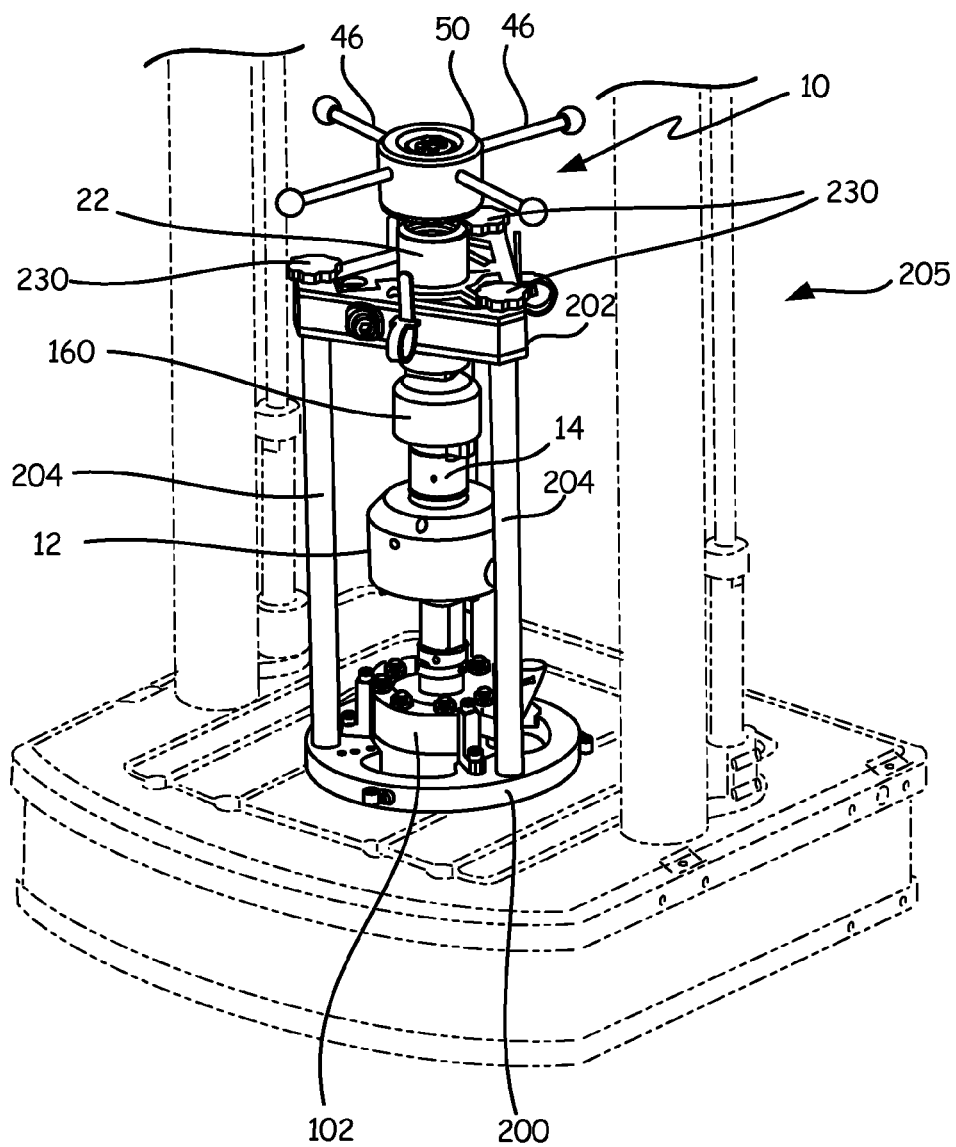
FIG. 2 is a perspective view of the force applicator assembly mounted to a test machine having a load cell.
Figure 5:
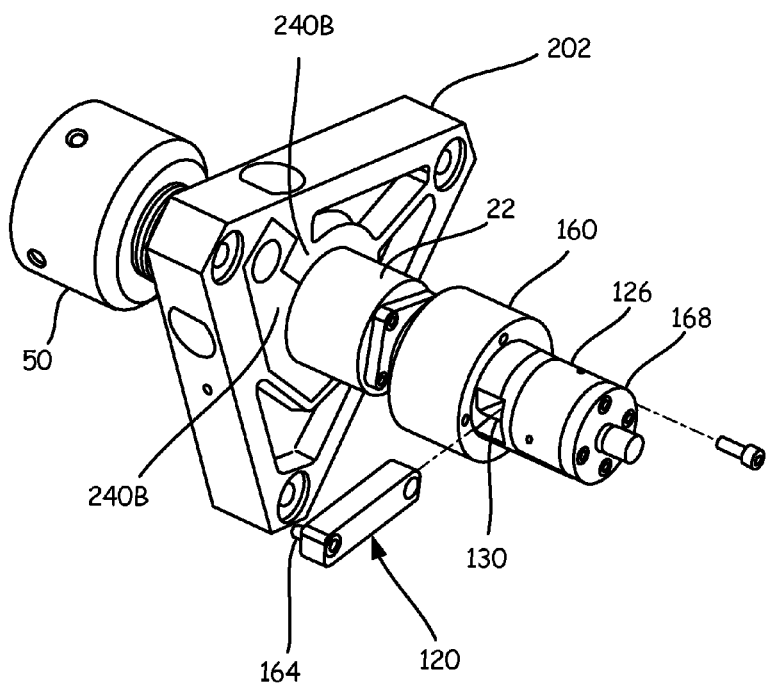
FIG. 5 is a perspective view of a portion of the force applicator assembly.

Referring to FIGS. 1 and 3, the reaction frame 18 includes a base member 200 and a reaction crosshead 202 supported over the base member 200 by vertical support(s) 204. The force applicator assembly is assembled in position to apply force loads to the load cell 102 by first installing the calibration standard 12 to the load cell under test 102 with the interface coupling 106. The base 200 is then mounted to the load frame or load machine 205 as illustrated in FIGS. 2 and 8 with the vertical supports 204 attached prior to mounting the base 200 to the load machine 205. Next, the force applicator 10 with the reaction cross-head 202 attached thereto is mounted to the vertical supports 204 herein with screw fasteners 230. In one embodiment, the reaction crosshead 202 comprises a clamp that is adjustably fixed to the stationary support 22 so as to provide gross positioning of the force applicator 10. In particular, the clamp is first set to the unclamped position allowing the force applicator 10 and coupler 14 to be rotated and translated threading the interface 168 into the load cell 104. Once a secure connection has been made between the coupler 14 and the load cell 104, the force applicator 10 is clamped to the reaction cross-head 202. FIGS. 5 and 6 illustrate clamping portions 240A and 240B that selectively engage the stationary support 22.

The force applicator 10 can be mounted in or on the machine without removal of the force transducer or load cell allowing in-situ calibrations. This allows for adherence with international standards for calibrations that require the transducer to be undisturbed. Furthermore, in one embodiment, in view of that the reaction structure 18 is secured to the testing machine, such as to the base as illustrated in FIG. 2 or 6, the remainder of the testing machine and in particular the crosshead of the testing machine, which can include the force actuator as shown in FIG. 2, does not need to be used to provide a reaction structure. This independence eliminates the parent machine quality as a source of error. The modular design allows for easy, step-wise installation. Embodiments can incorporate alignment features that facilitate repeatability accurate installation and results. It should be understood that mounting of the force applicator so as to perform in-situ calibration of a load cell or force transducer mounted to the base of the testing machine is not limiting. In another application, the force applicator can be operably connected to an in-situ load cell that is mounted to an actuator applying loads in any orientation. For example, if the actuator is mounted to the base and in-situ load cell is mounted to actuator, the force applicator can be operably coupled to the in-situ load cell. If a reaction structure 18 is needed, it can be secured to the actuator or a support for the actuator in any manner. Likewise, if the if the actuator is mounted to a cross-head, which can be movable as necessary to conduct a test, and an in-situ load cell is mounted to actuator, the force applicator can be operably coupled to the in-situ load cell. If a reaction structure 18 is needed, it can be again secured to the actuator or a support, such as the cross-head, for the actuator in any manner. When it is desired to test the in-situ load cell, the force applicator 10 can be operated to achieve the afore-described spaces between the curved members 122A, 122B and the reaction structure 120 when it is necessary to have a state where no tension or compression loads are being applied.

Although the subject matter has been described in language specific to structural features and/or methodological acts, it is to be understood that the subject matter defined in the appended claims is not necessarily limited to the specific features or acts described above as has been held by the courts. Rather, the specific features and acts described above are disclosed as example forms of implementing the claims.

What is claimed is:

1. A coupling assembly to couple a first element to a second element to transfer linear compression and/or tension forces, the coupling assembly comprising:
   a retainer assembly connectable to the first element, the retainer assembly having a first member having a first three dimensional curved surface and a second member having a second three dimensional curved surface spaced apart from and facing the first three dimensional curved surface; and
   a reaction structure connectable to the second element, the reaction structure disposed between the first and second three dimensional curved surfaces, the reaction structure and spacing between the first and second three dimensional curved surfaces configured such that movement of the second element causes the reaction structure to contact only one of the first or second three dimensional curved surfaces at a time when transmitting forces from the second element to one of the first and second three dimensional surfaces.

2. The coupling assembly of claim 1 wherein each of the first and second three dimensional curved surfaces comprises at least a partial ball.

3. The coupling assembly of claim 1 wherein the retainer assembly includes at least one aperture, the reaction structure extending through the aperture.

4. The coupling assembly of claim 1 wherein the retainer assembly includes opposed apertures, the reaction structure extending through each of the apertures.

5. The coupling assembly of claim 1 wherein the reaction structure includes opposed concave surfaces, each concave surface engaging one of the three dimensional curved surfaces.

6. The coupling assembly of claim 1 wherein the first and second three dimensional curved surfaces comprise convex surfaces arranged to protrude toward each other.

7. The coupling assembly of claim 1 wherein the first element comprises a load cell.

8. The coupling assembly of claim 7 and further comprising:
   a reference load cell aligned with the load cell.

9. The coupling assembly of claim 1 wherein the second element comprises a moving member of an actuator assembly.

10. The coupling assembly of claim 1 wherein a distance between the three dimensional curved surfaces is greater than a width of the reaction structure.

11. The coupling assembly of claim 1 wherein the retainer assembly includes at least one aperture, the reaction structure extending through the aperture, wherein a distance between the three dimensional curved surfaces is greater than a width of the reaction structure, and wherein one or more spaces between the first and second members and the reaction structure can be seen from a vantage point external to the coupling assembly.

12. A coupling assembly to couple a first element to a second element to transfer linear compression and/or tension forces, the coupling assembly comprising:
   a retainer assembly connectable to the first element, the retainer assembly including:
      a first member having a first convex partially spherical surface; and
      a second member having a second convex partially spherical surface spaced apart from and facing the first convex partially spherical surface such that the first and second convex partially spherical surfaces protrude toward each other; and
   a reaction structure connectable to the second element, wherein the reaction structure is disposed between the first and second convex partially spherical surfaces of the retainer assembly, wherein the reaction structure and spacing between the first and second convex partially spherical surfaces are configured such that movement of the second element causes the reaction structure to contact only one of the first or second convex partially spherical surfaces at a time when transmitting forces from the second element to one of the first and second convex partially spherical surfaces, and wherein the coupling assembly is configured to align an axis of the first element with an axis of the second element when forces are transferred through the coupling assembly.

13. The coupling assembly of claim 12 wherein the retainer assembly includes opposed apertures, the reaction structure extending through each of the apertures.

14. The coupling assembly of claim 12 wherein the reaction structure includes opposed concave surfaces, each concave surface engaging one of the convex partially spherical surfaces.

15. The coupling assembly of claim 12 wherein the first element comprises a load cell.

16. The coupling assembly of claim 15 and further comprising:
   a reference load cell aligned with the load cell.

17. The coupling assembly of claim 12 wherein the second element comprises a moving member of an actuator assembly.

18. The coupling assembly of claim 12 wherein a distance between the first and second convex partially spherical surfaces is greater than a width of the reaction structure.

19. The coupling assembly of claim 12 wherein the retainer assembly includes at least one aperture, the reaction structure extending through the aperture, wherein a distance between the first and second convex partially spherical surfaces is greater than a width of the reaction structure, and wherein one or more spaces between the first and second convex partially spherical surfaces and the reaction structure can be seen from a vantage point external to the coupling assembly.

20. The coupling assembly of claim 12 wherein the retainer assembly includes at least one aperture, the reaction structure extending through the aperture.

* * * * *